(12) United States Patent
Dinkelacker (10) Patent No.: US 6,364,663 B1
(45) Date of Patent: Apr. 2, 2002

(54) TOOTH IMPLANT AND METHOD TO MAKE IT

(76) Inventor: Wolfgang Dinkelacker, Mercedesstr. 9/1, 71063 Sindelfingen (DE)

(*) Notice: Subject to any disclaimer, the term of this patent is extended or adjusted under 35 U.S.C. 154(b) by 0 days.

(21) Appl. No.: 09/454,897

(22) Filed: Dec. 3, 1999

(30) Foreign Application Priority Data

Dec. 11, 1998 (EP) .......................................... 98 123 681

(51) Int. Cl.[7] .............................................. A61C 8/00
(52) U.S. Cl. ..................................................... 433/173
(58) Field of Search .................................. 433/173, 174, 433/175, 176, 177

(56) References Cited

U.S. PATENT DOCUMENTS

| | | | |
|---|---|---|---|
| 4,185,383 A | * 1/1980 | Heimke et al. | 433/173 |
| 4,599,085 A | * 7/1986 | Riess et al. | 433/173 |
| 5,195,891 A | * 3/1993 | Sulc | 433/173 |
| 5,209,659 A | * 5/1993 | Friedman et al. | 433/173 |
| 5,310,343 A | * 5/1994 | Hasegawa et al. | 433/173 |
| 5,344,457 A | * 9/1994 | Pilliar et al. | 433/174 |
| 5,413,480 A | * 5/1995 | Musikant et al. | 433/173 |
| 5,503,558 A | * 4/1996 | Clokie | 433/173 |
| 5,564,923 A | * 10/1996 | Grassi et al. | 433/173 |
| 5,620,323 A | * 4/1997 | Bressman et al. | 433/174 |
| 5,762,499 A | * 6/1998 | Dard et al. | 433/173 |
| 5,820,374 A | 10/1998 | Simmons et al. | |
| 5,829,978 A | * 11/1998 | Day | 433/174 |
| 5,989,027 A | * 11/1999 | Wagner et al. | 433/173 |

FOREIGN PATENT DOCUMENTS

| | | |
|---|---|---|
| DE | 35 33 395 A1 | 5/1986 |
| DE | 3811498 | 10/1989 |
| DE | 3839724 | 5/1990 |
| DE | 40 00 112 A1 | 7/1991 |
| DE | 4130891 | 3/1992 |
| DE | 29707545 | 10/1997 |
| EP | 139 253 B1 | 5/1985 |
| EP | 388 576 B1 | 9/1990 |
| FR | 2715568 | 8/1995 |
| WO | WO 96/16611 | 6/1996 |

OTHER PUBLICATIONS

Cochran, D.L. et al.; "Bone response to unloaded and loaded titanium implants with a sandblasted and acid–etched surface: A histometric study in the canine mandible"; Journal of Biomedical Materials Research, v. 40, 1998, pp. 1–11, John Wiley & Sons, Inc.

* cited by examiner

Primary Examiner—Ralph A. Lewis
(74) Attorney, Agent, or Firm—Kudirka & Jobse, LLP (57) ABSTRACT

The surface of a cylindrical, conical or stepped tooth implant has numerous groove-shaped recesses along its lengthwise axis or at a sharp angle to it. An alternative embodiment provides crosswise groove-shaped recesses at a sharp angle. In another embodiment, the surface of the implant body is divided along its lengthwise axis into numerous sections or steps that are separated by radial bands or transitions. The sections or steps have numerous groove-shaped recesses in their perimeter that follow the lengthwise axis of the implant body or run at a sharp angle or crosswise at a sharp angle. To create the tooth implant, a cylindrical, conical or stepped implant body with a smooth surface is preformed by creating groove-shaped recesses in a material-removing process. The material removing process is advantageously carried out with a digitally-controlled laser beam.

77 Claims, 10 Drawing Sheets

TOOTH IMPLANT AND METHOD TO MAKE IT

SCOPE OF THE INVENTION

The invention concerns a tooth implant that can be inserted in the jaw in an operation with a rotationally-symmetrical implant body that has a rough surface, and a method to make the implant.

STATE OF THE ART

Prior-art tooth implants have a rotationally-symmetrical implant body that can be designed as a cylinder or cone or as a stepped shape. The implant body consists of titanium that is very biologically compatible with the bone tissue. The surface of the implant body, such as a coating with hydroxylapatite (DE A 38 39 724), promotes stable healing where it contacts the bodily tissue. It is also prior art that the surfaces of the implant body are exposed to an acidic etching process after the natural titanium oxide layer is removed to attain an essentially uniform roughness over the entire surface (WO 96/16611).

By treating the surface of the implant body, contact with the surrounding bone tissue is made easier, and the participating implant surface is increased. A titanium plasma coating (TPC) is prior art that is created by thermal spraying titanium onto the titanium implant. In addition, a process is used that treats the surface by coarse sand blasting to create macroroughness in the titanium. This process is followed by acid etching that generates evenly-distributed micropits in the sand-blasted surface (Cochran et al., "Bone response to unloaded and loaded titanium implants with a sand-blasted and acid-etched surface", Journal of Biomedical Materials Research, Vol. 40, 1998, p.1).

The osteons of the bone only collect slightly on the surface of the implant body or not at all. The biomechanical integration of the implant is hindered.

The goal of the invention is to design the surface of the implant to improve the bone deposition and hence achieve long-term biomechanical integration of the implant in the jawbone. The subject of the invention is also a method to produce such a surface.

SUMMARY OF THE INVENTION

According to the invention as defined in claims 1, 12 and 27, the surface of the implant body has numerous groove-shaped recesses that follow its lengthwise axis or are at a sharp angle to it.

The histology of bone reveals a lamellar structure that is composed of an outer general lamella with embedded osteocytes that are 2–3 micrometers large, osteons (Havers systems) with special lamella 20–300 micrometers large, intermediate lamellae that contain dead and partially transformed osteons, and an inner general lamella. The osteons are surrounded by collagen that form helically around the Havers channel like a tree structure and are embedded in the bone substance. The osteons are aligned according to the static tasks of the bone.

The invention allows the osteons of the bone to attach to the groove-shaped recesses of the implant surface and grow along the implant. The size of furrows formed by the trough-shaped recesses is adapted to the size of the osteons, and the furrows accept the parts of the osteons that come into contact with the implant. As a result and due to the pressure acting on the implant, compact bone is formed around the implant in the spongiosa area of the bone that better absorbs the forces acting on the implant and provides a stable and permanent seat for the implant.

This effect is reinforced in that there are numerous, small, densely-distributed concave recesses in the trough-like recesses. The concave recesses accept the osteocytes of the bone tissue surrounding the implant and hence support the contact between the implant and bone.

Crosswise groove-like recesses improve the osteon deposition. A first set of grooves is provided that runs in a first direction at a sharp angle to the lengthwise axis of the implant body, and a second set of grooves is provided that runs in a second direction at a sharp angle to the lengthwise axis of the implant body and that cross the first grooves. The trough-like recesses are advantageously close together and have a concave profile whose edges run into the perimeter of the implant body. Such a surface structure offers favorable conditions for osteons to collect during the healing phase and additionally secure against axial shifting and rotation of the implant after healing.

In another embodiment of the invention, the surface of the implant body along its lengthwise axis is divided into numerous sections that are separated by radial bands. The perimeter of the sections has numerous groove-shaped recesses that run in the direction of the lengthwise axis of the implant body or at a sharp angle to it. The bands assume the function of barriers during the healing and healed stages against any foci descending from the head of the implant. The diameter of the sections can differ and decrease stepwise toward the bottom end of the implant body. The diameter of the implant body narrows in the area of the radial bands. Likewise, the surface structure of the sections can also differ. These features essentially contribute to a fixed seat for the implant in the jawbone and offer favorable conditions for the deposition of osteons in the grooves of each of the sections.

A procedure to manufacture a tooth implant according to the invention provides that numerous groove-shaped recesses that run along the lengthwise axis are created in the surface of the implant body by a material removal process in one of the smooth implant bodies preformed into the desired shape. The material removal process is advantageously carried out by a digitally-controlled laser beam. Instead of a laser beam, a focused ion beam can be used. Alternately, the material removal process can also be carried out by a precision milling machine.

In another step, troughs or "lagoons" are introduced into the surface of the implant body that are small in comparison to the groove-shaped recesses. This step can consist of acid etching. The head and in certain cases the foot of the implant can be covered with an acid-resistant coating. A digitally-controlled laser beam can also be used to introduce the troughs or lagoons so that the same material removal process can be used to create both the groove-shaped recesses and troughs or lagoons.

DESCRIPTION OF THE DRAWINGS

In the following, various embodiments of the invention will be discussed with reference to drawings. Shown are.

DETAILED DESCRIPTION OF THE EXEMPLARY EMBODIMENT OF THE INVENTION PORTRAYED IN THE DRAWING

Figure 1:
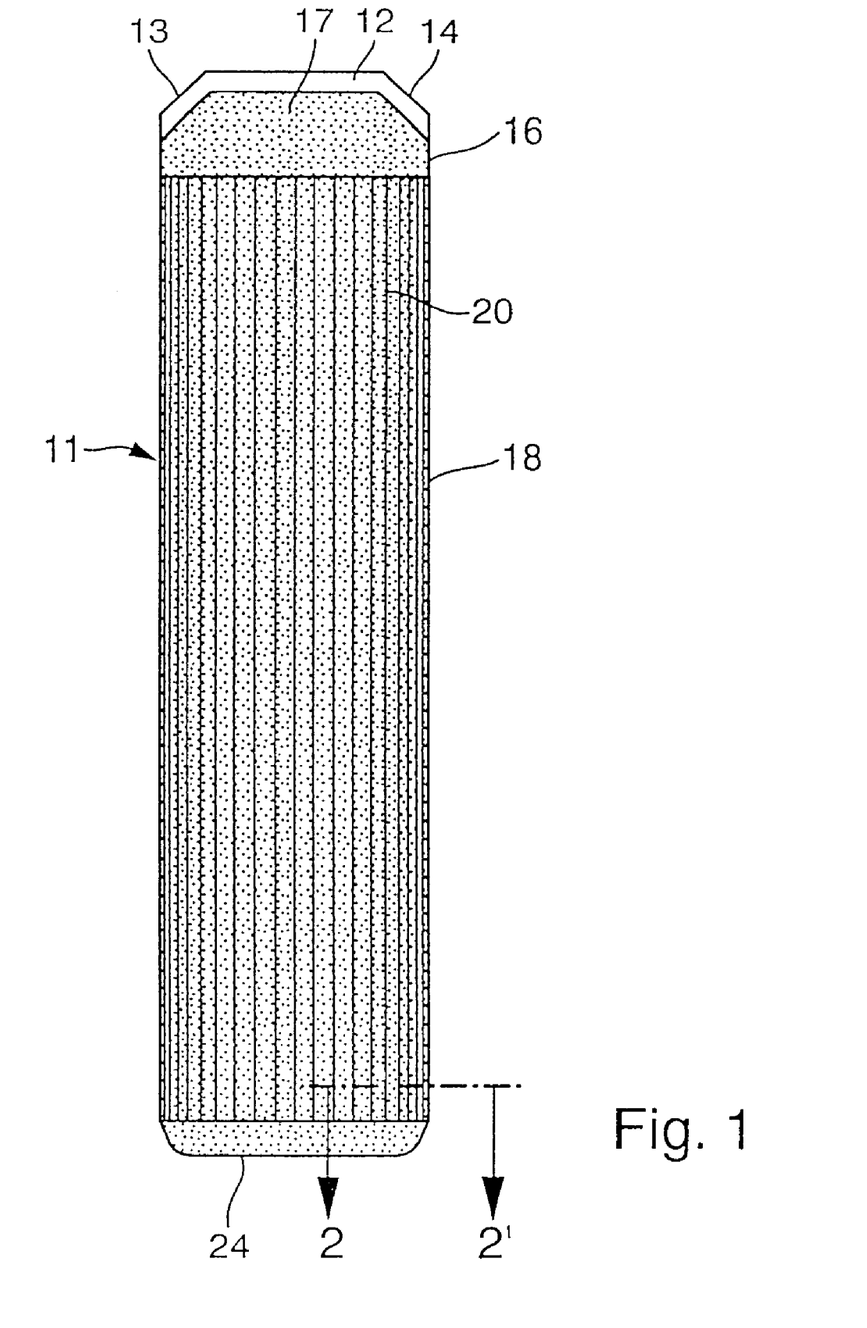
FIG. 1 A cylindrical tooth implant with axial grooves,
FIG. 2 A partial section along line 2–2' in FIG. 1,
FIG. 3 An enlarged view of a part of FIG. 1,
FIG. 4 A partial section along line 4–4' in FIG. 3,
FIG. 5 An enlarged section of another part of FIG. 1,
FIG. 6 A partial section along line 6–6' in FIG. 3,
FIGS. 7A, 7B and 7C Enlarged top views of the groove-shaped recesses as they are used in the tooth implant in FIG. 1, FIG. 8 A conical tooth implant with cross-wise grooves, FIG. 9 A tooth implant in a stepped conical shape with axial grooves FIG. 10 A tooth implant in a stepped conical shape with crosswise grooves FIG. 11 A cylindrical tooth implant with axial grooves divided into sections, FIGS. 12, 13 Conical tooth implant with axial grooves or crosswise grooves that are divided into sections, FIG. 14 A tooth implant in a stepped conical shape with axial grooves in the area of the individual steps, p FIG. 15 A tooth implant in a stepped conical shape with grooves that are at a sharp angle to the lengthwise axis of the implant in the perimeter of the individual steps, FIG. 16 A tooth implant in a stepped conical shape with crosswise groove in the perimeter of the individual steps, FIG. 17 A tooth implant in a stepped conical shape with surface structures that run in different directions in the area of the individual steps, FIG. 18 A tooth implant in a stepped conical shape after the jawbone has healed.

The tooth implant in FIG. 1 comprises a cylinder 11 that consists of titanium which has a head 12 with a polished surface. The head 12 can be equipped with bevels 13, 14 on the bucal and lingual side as shown in EP A 0 868 889 that serve to receive supports (not shown) for a tooth crown. Below the head 12 is a collar 16 that has numerous small troughs or lagoons 17 in its perimeter. Abutting the collar 16 is a body area 18 that extends over the majority of the length of the implant cylinder 11. The body area 18 has closely adjacent groove-shaped recesses 20 in its perimeter that run in an axial direction (also termed furrows). The recesses 20 advantageously have a concave profile (FIG. 2) whose edges end at the perimeter of the body area 18 and form a rounded comb 22 with each of the two neighboring recesses. The groove-shaped recesses are 20–300 μm wide and 10–150 μm deep. During the healing phase, the osteons of the bone tissue can collect in the groove-shaped recesses. The width of the grooves corresponds to the dimensions of the osteons.

The entire surface of the body area 18 is also provided with numerous small troughs or lagoons whose average diameter is advantageously around 3 μm and whose depth is advantageously around 1 μm, and that supports the implant as it grows in. At its bottom, the cylinder 11 is terminated by a rounded foot 24 that also has numerous small troughs or lagoons in its surface.

Figure 3:
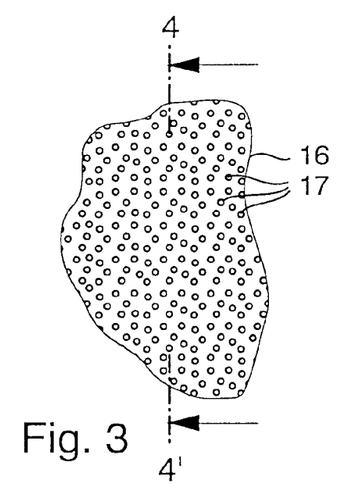
Figure 4:
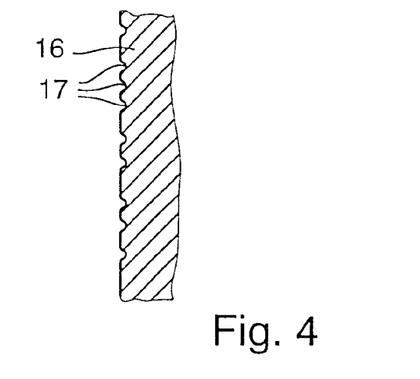
Figure 5:
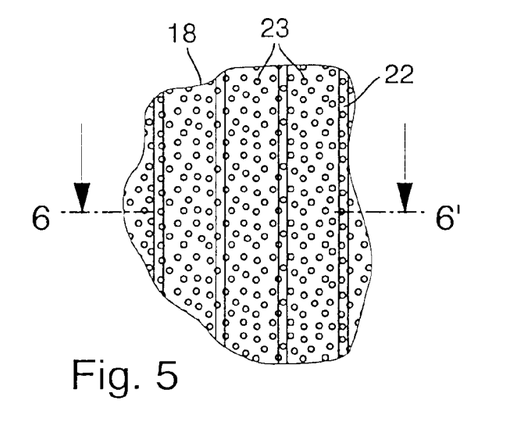
Figure 6:
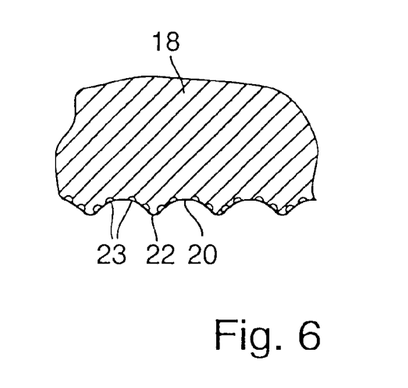

FIGS. 3–6 show enlarged troughs or lagoons at areas 16, 18, and 24 of the cylinder 11. FIG. 3 is an enlarged section of the surface of the collar 16. The section shows numerous small, sharply delimited concave troughs 17 that are densely distributed over the surface of the collar 16. The troughs 17 reinforce the blocking effect of the collar 16 against the penetration of bacteria from the throat into the receiving channel of the implant. The sectional view in FIG. 4 shows the concave profile of the troughs 17 that are created by acid etching or a laser, as will be described. A surface structure as shown in FIGS. 3 and 4 is also found in the foot 24 of the cylinder 11. FIGS. 5 and 6 show the arrangement of corresponding troughs in the perimeter of the body area 18. FIG. 5 shows an enlarged section of the surface of the body area 18. The section shows numerous sharply delimited, concave troughs 23 that are densely distributed over the surface of the groove-shaped recesses 20 and the combs 22. The section in FIG. 6 shows the concave profile of the troughs 23.

Figure 2:
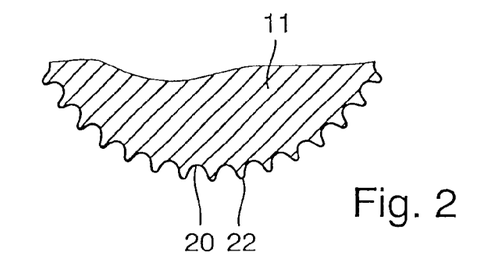
Figure 7A:
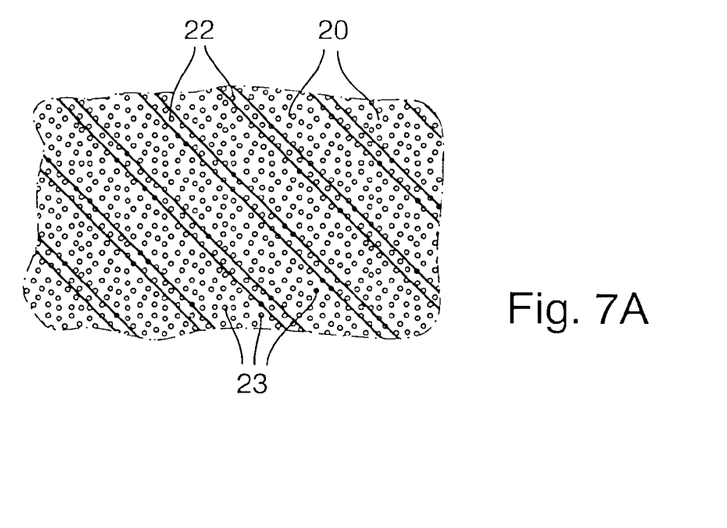
Figure 7B:
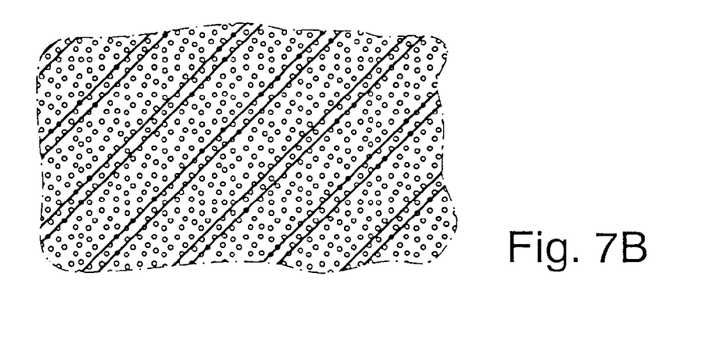
Figure 7C:
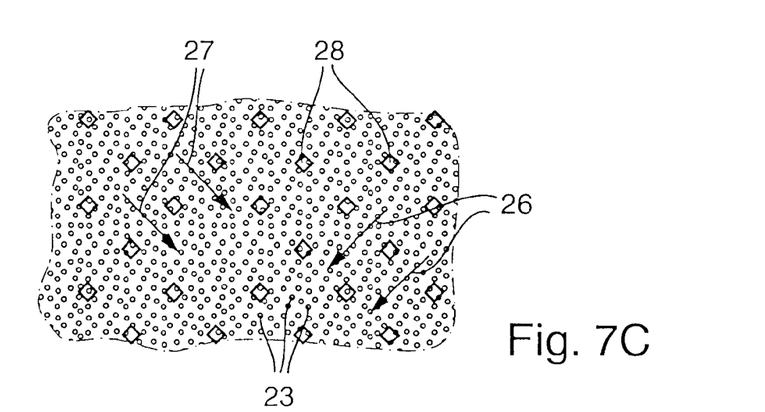

In deviation from the shape in FIG. 1, the groove-shaped recesses 20 can run at a sharp angle to the lengthwise axis of the implant, e.g. at a 45° angle so that a groove path arises as shown in FIGS. 7A and 7B that winds to the right or left in an enlarged top view of a section of the body area of a correspondingly designed tooth implant. FIG. 7C shows a crosswise path of the grooves. In this design, initial grooves are provided that run in a first direction 26 in FIG. 7C to the left at a sharp angle to the lengthwise axis of the implant body. Second grooves are provided that run in a second direction 27, i.e., to the right at a sharp angle to the lengthwise axis of the implant body, and they intersect with the first grooves to produce numerous knob-shaped, rounded bumps 28 that are evenly distributed over the surface of the body area 18. The groove structures in FIGS. 7A, 7B and 7C advantageously have a profile as shown in FIG. 2 and offer favorable conditions for the osteons to collect during the healing phase, and they offer an additional hold against axial shifting and rotation of the implant when ingrown.

Additional small troughs or lagoons 23 can be in the groove-shaped recesses that are small in contrast to the grooves and are densely distributed over the surface of the body area as shown in FIGS. 5 and 6. The troughs or lagoons 23 assist the anchoring of the implant in the jawbone by allowing a large number of osteocytes to collect on the surface of the body area.

Figure 8:
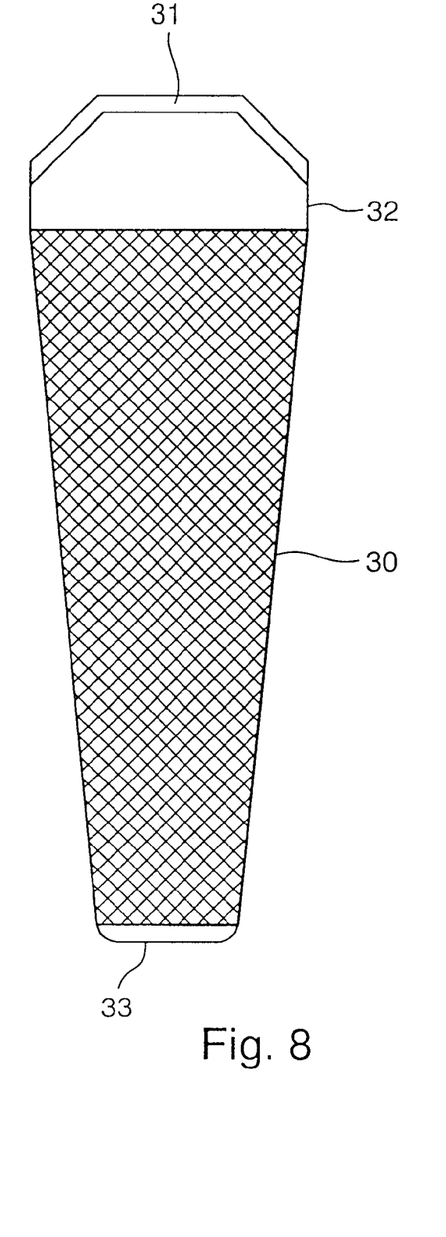

FIG. 8 shows a modification of the tooth implant in FIG. 1. In this embodiment, the body area 30 is conical and has a surface structure as in FIG. 7C with crosswise grooves as in FIG. 7C that are schematically drawn in FIG. 8. A head 31 and a collar 32 of t implant body in FIG. 8 that consists of titanium like the implant body of the exemplary embodiment of the invention described in the following corresponds to the areas 12 and 16 in FIG. 1. Contrasting to FIG. 1, the foot 33 of the implant in FIG. 8 can be polished smooth when it is used in conjunction with a sinus lift operation.

Figure 9:
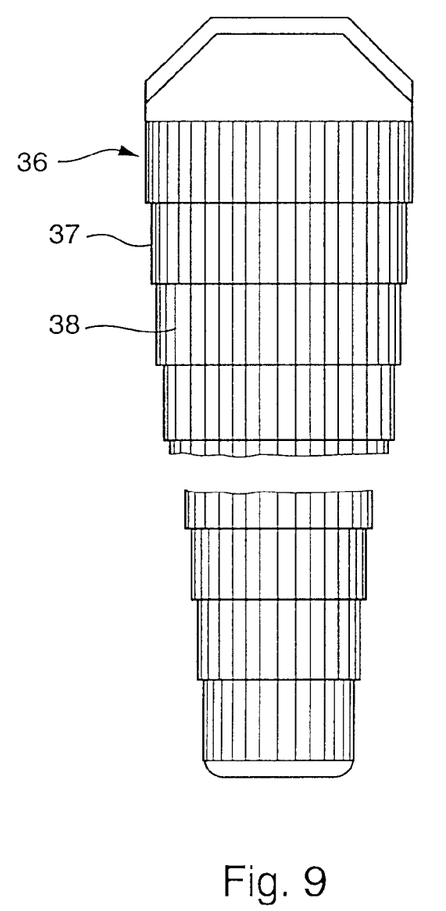
Figure 10:
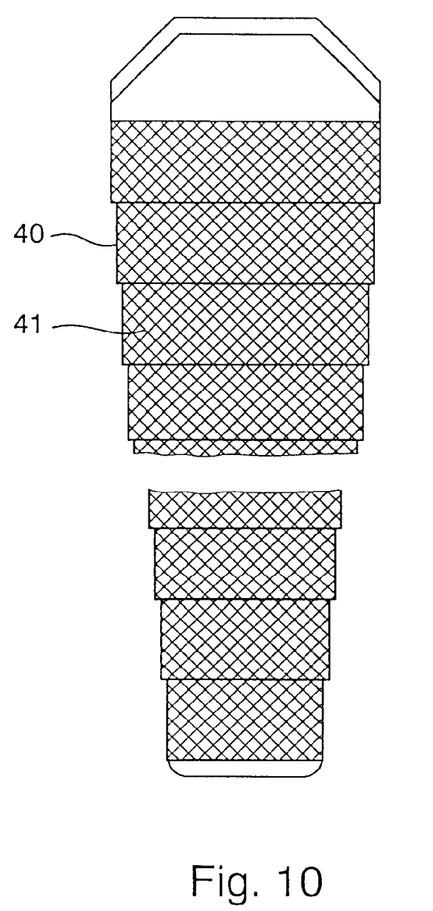

FIGS. 9 and 10 show exemplary embodiments of the tooth implant according to the invention in which the body narrows downward in steps. Numerous steps can be provided. The step height is preferably around 20–300 μm. The perimeter of each step is provided with a groove structure as in FIGS. 7A, 7B or 7C. FIG. 9 shows a tooth implant with a body 36 in which the perimeter of each step 37 has grooves 38 that follow the lengthwise axis of the implant body and advantageously are the same width over all the steps 37. This produces a different number of grooves 38 in each step, and the grooves of each step are at an offset angle in contrast to the grooves of the prior step. At the head, collar and foot, the implant in FIG. 9 corresponds to that in FIG. 8. The implant in FIG. 10 differs from the implant in FIG. 9 in that the perimeter of each step 40 is provided with a crossing groove structure 41 as in FIG. 7C that is schematically drawn in FIG. 10.

Figure 11:
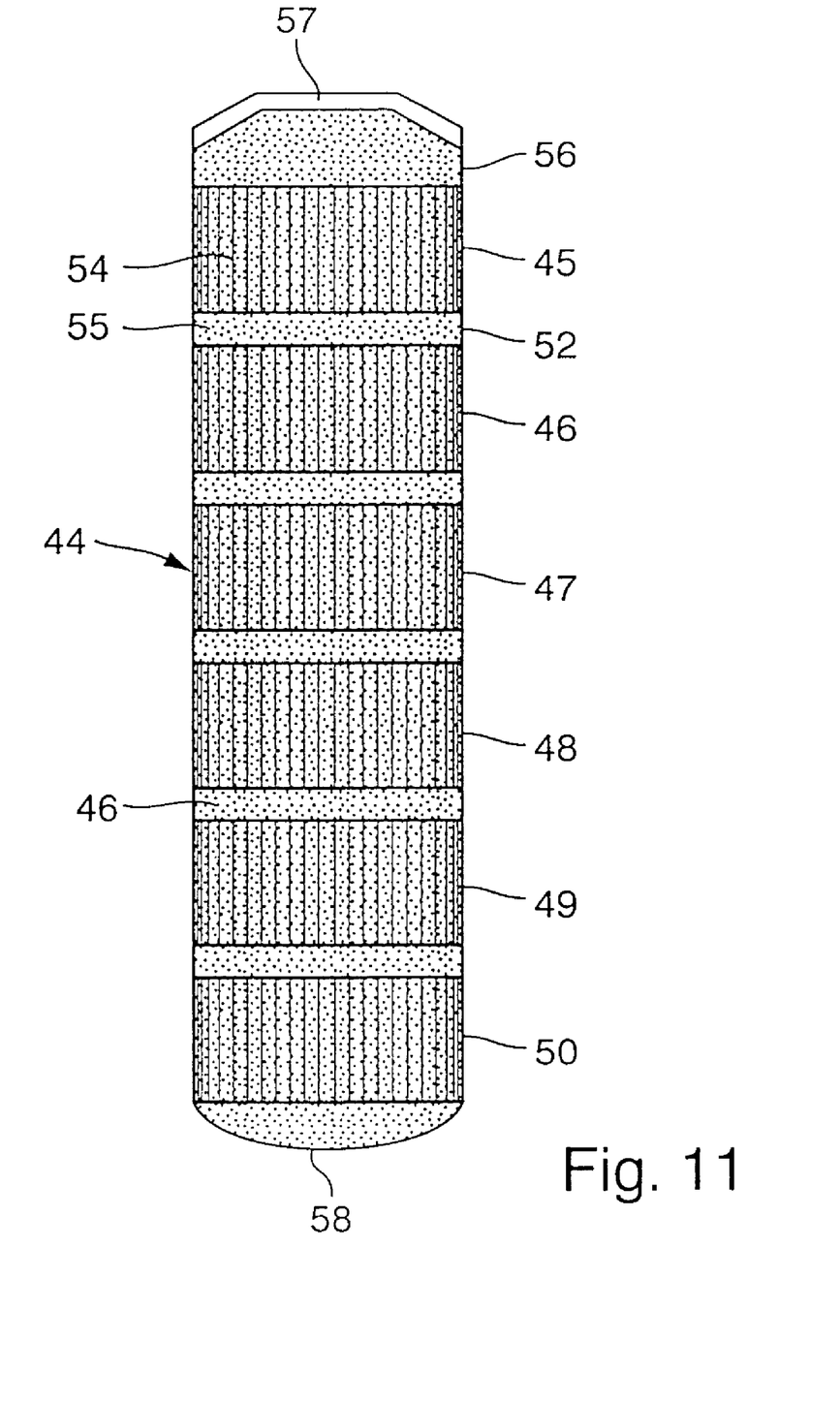

Other embodiments of the tooth implant according to the invention are shown in FIGS. 11–17. FIG. 11 shows a cylinder 44 made of titanium that is divided into a number of sections 45–50. Each two neighboring sections 45–50 are separated by a narrow band 52 that serves as a barrier against foci penetrating from above from the throat; it is hence also termed a barrier area. The perimeter of each of the sections 45–50 has closely-adjacent, axial groove-shaped recesses 54 that preferably have the concave profile as shown in FIG. 2. Instead of the axial recesses, the sections 45–50 can also have angled or crosswise grooves of the kind in FIGS. 7A, 7B and 7C. The perimeter of each of the separating or barrier areas 52 has numerous small troughs 55 as in FIGS. 3 and 4 that support the barrier effect against bacteria. Likewise, the sections 45–50 are provided with troughs as in FIGS. 5 and 6 that are smaller compared to the dimensions of the recesses 54. The collar 56 that is between the top section 45 and a polished head 57 has the cited troughs. At the bottom, the cylinder 44 terminates in a rounded foot 58 that is highly polished for special uses like a sinus lift.

Figure 12:
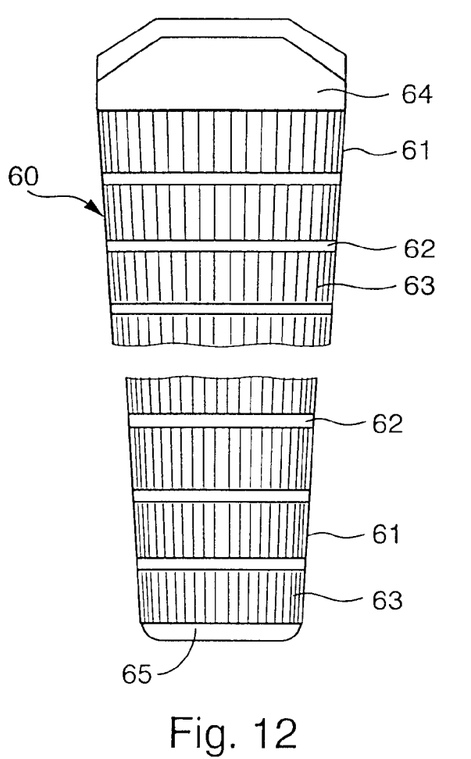
Figure 13:
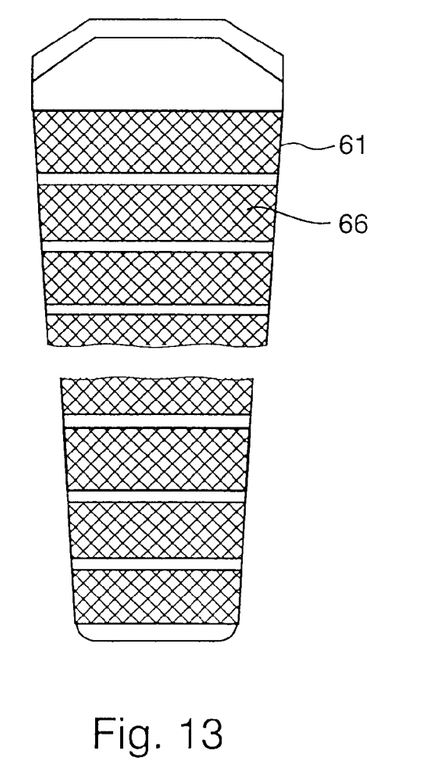

FIGS. 12 and 13 show corresponding conical embodiments. FIG. 12 shows the body of a conical tooth implant 60 divided into sections 61 of which every two are separated by a barrier 62. The sections have grooves 63 that run in the lengthwise direction of the cone and follow the lengthwise direction of the conical surface. The grooves 63 are preferably arranged so that they have the same width at the start of each section 61 viewed from top to bottom, and their width and depth decrease downward. The surface of the barriers 62 are provided with numerous small troughs as in FIGS. 3 and 4 like the surfaces of the collar 64 at the top end of the implant 60 and foot 65. Corresponding troughs are in the area of the grooves 63 as in FIGS. 3 and 4. The embodiment in FIG. 13 differs from the embodiment in FIG. 12 in that the sections 61 have a groove arrangement as in FIG. 7C where grooves 66 cross at a sharp angle to the cone axis to the left and right in each section. FIG. 13 schematically portrays these grooves.

Figure 14:
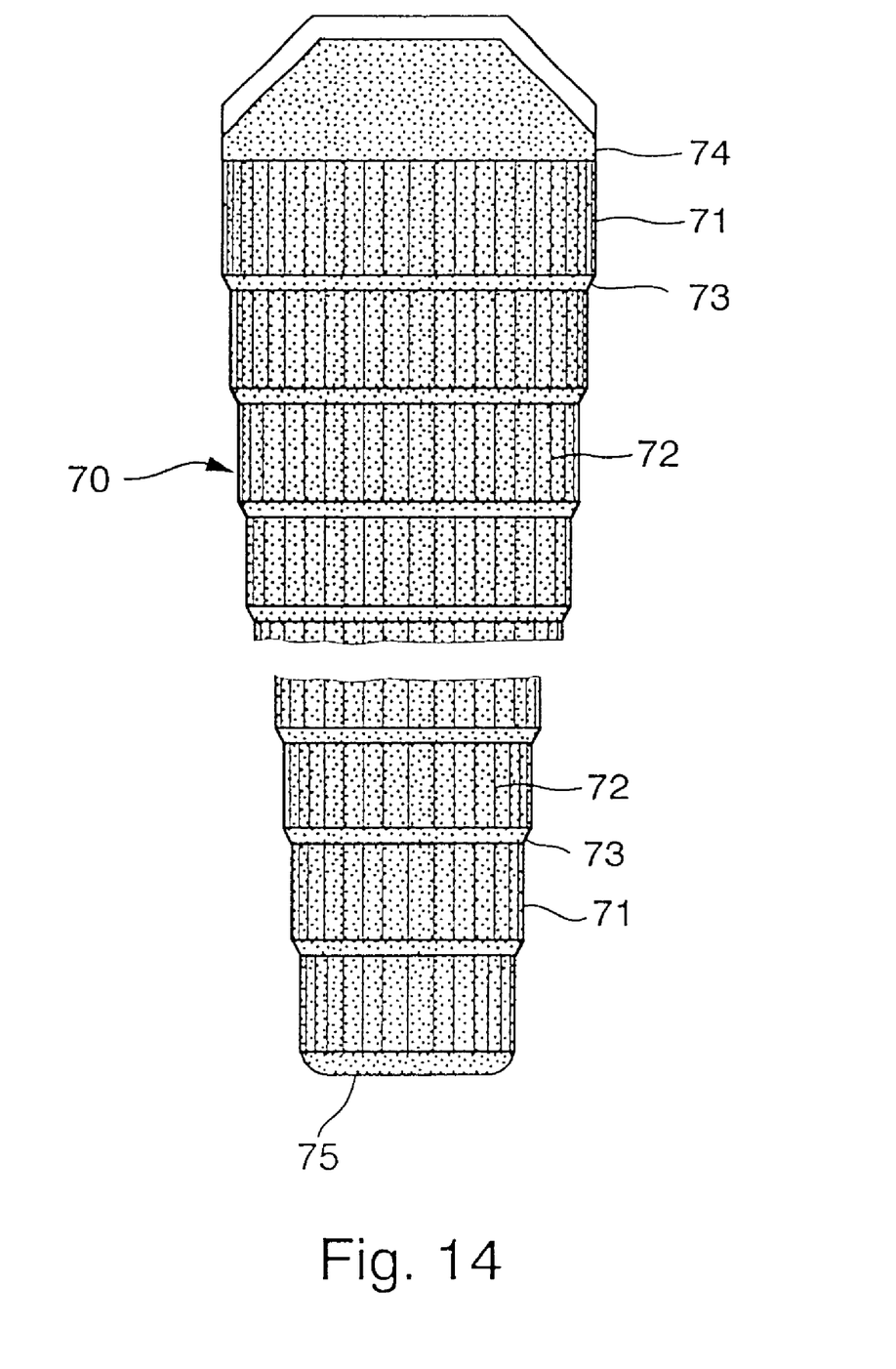
Figure 15:
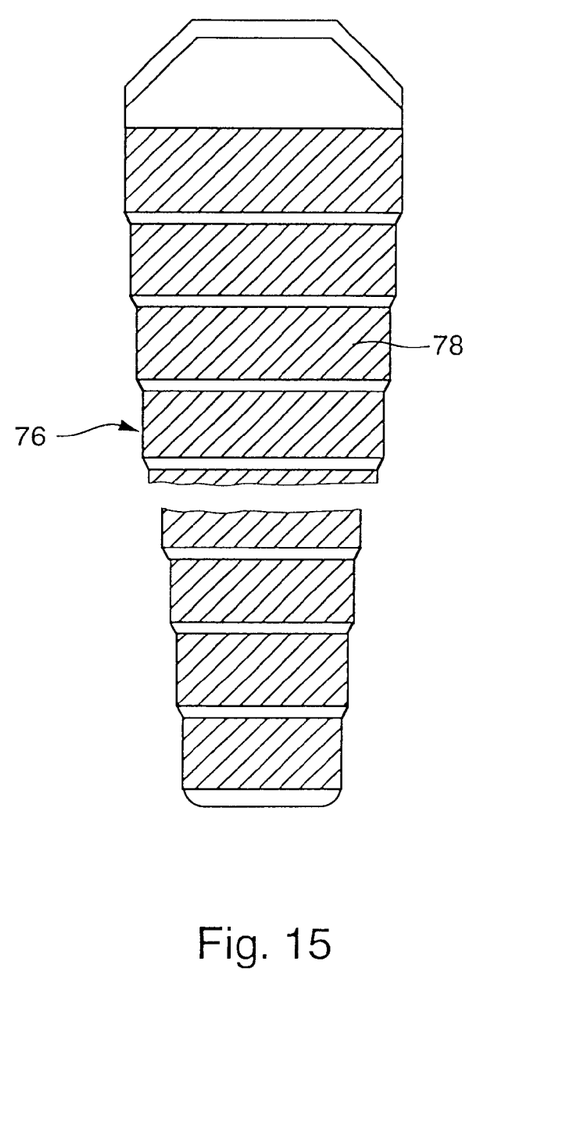
Figure 16:
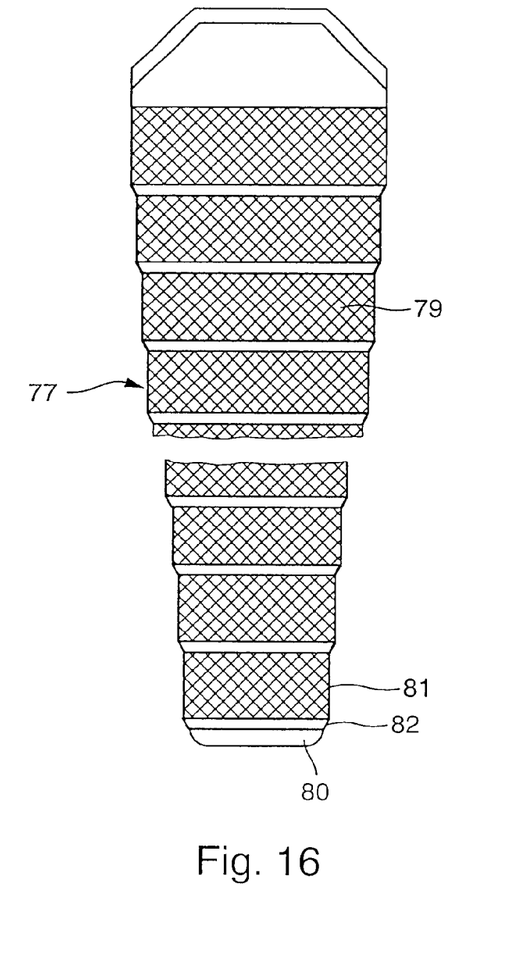

FIGS. 14–17 show embodiments of the invention in which the body of a rotationally-symmetrical implant body narrows downward in steps. A conical area separates every two of the steps. The perimeter of each step is provided with a groove structure as in FIGS. 7A, 7B or 7C. FIG. 14 represents a tooth implant with a body 70 that is divided into numerous steps 71. Each of the steps 71 has grooves 72 that follow the lengthwise axis of the implant body. Between each two steps 71 is a conical transition area 73 that is narrow in relation to the length of the steps 71 and that acts as a barrier in the manner described above. The grooves 72 advantageously are the same width over all the steps 71. The number of grooves 72 in each of the steps 71 differs, and the grooves of each step are at an offset angle to the grooves of the prior step. The surface of the steps 71, transition 73, collar 74, and foot 75 are provided with numerous small troughs of the kind in FIGS. 3–6. FIG. 15 shows a corresponding implant body 76 in which the steps 71 have angled grooves 78 as in FIG. 7B, and FIG. 16 schematically shows a corresponding implant body 77 that has crosswise grooves 79 as in FIG. 7C. The implant body 77 in FIG. 16 also has a polished foot 80 that is connected with the bottom step 81 by a polished conical transition 82.

Figure 17:
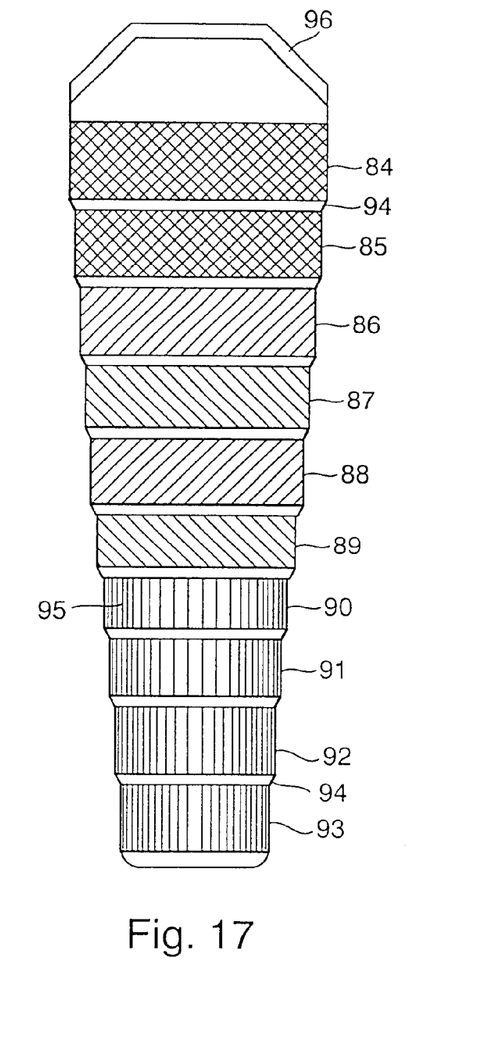

FIG. 17 shows an embodiment of the tooth implant according to the invention as in FIG. 14 in which at least one part of the steps has different groove structures. The body of the implant in FIG. 17 is divided into ten steps 84–93 that are connected by transition areas 94. The perimeter of the two top steps 84 and 85 have crosswise grooves as in FIG. 7C. Of the steps 86 and 87 that follow below, step 86 has grooves that run left at a sharp angle to the lengthwise axis of the implant, and step 87 has grooves that run right at a sharp angle to the lengthwise axis of the implant. The surface structure of the next steps 88 and 89 corresponds to that of steps 86 and 87, while all the other steps 90–93 have grooves 95 that run in an axial direction. The width of the grooves can differ in the individual steps. Steps 90–93 that are surrounded by a porous bone tissue can be wider than the steps above them. The entire surface of the implant in FIG. 17 is covered with troughs or lagoons of the kind in FIGS. 3–6 with the exception of a head area 96 that has a smooth and polished surface.

The surface structure that alternates over steps 84–93 takes into account the different density of the bone that surrounds the implant over its length. In particular, the two top steps 84, 85 with their crosswise grooves form a good anchor for the implant in the compact bone and the neighboring area, while the surfaces of the following steps can be adapted to the downwardly-increasingly porous bone tissue. The combination of different surface structures over the implant body also helps to better secure the implant during the healing and healed phases against axial shifting and rotation, and to better conduct pressure into the bone.

Figure 18:
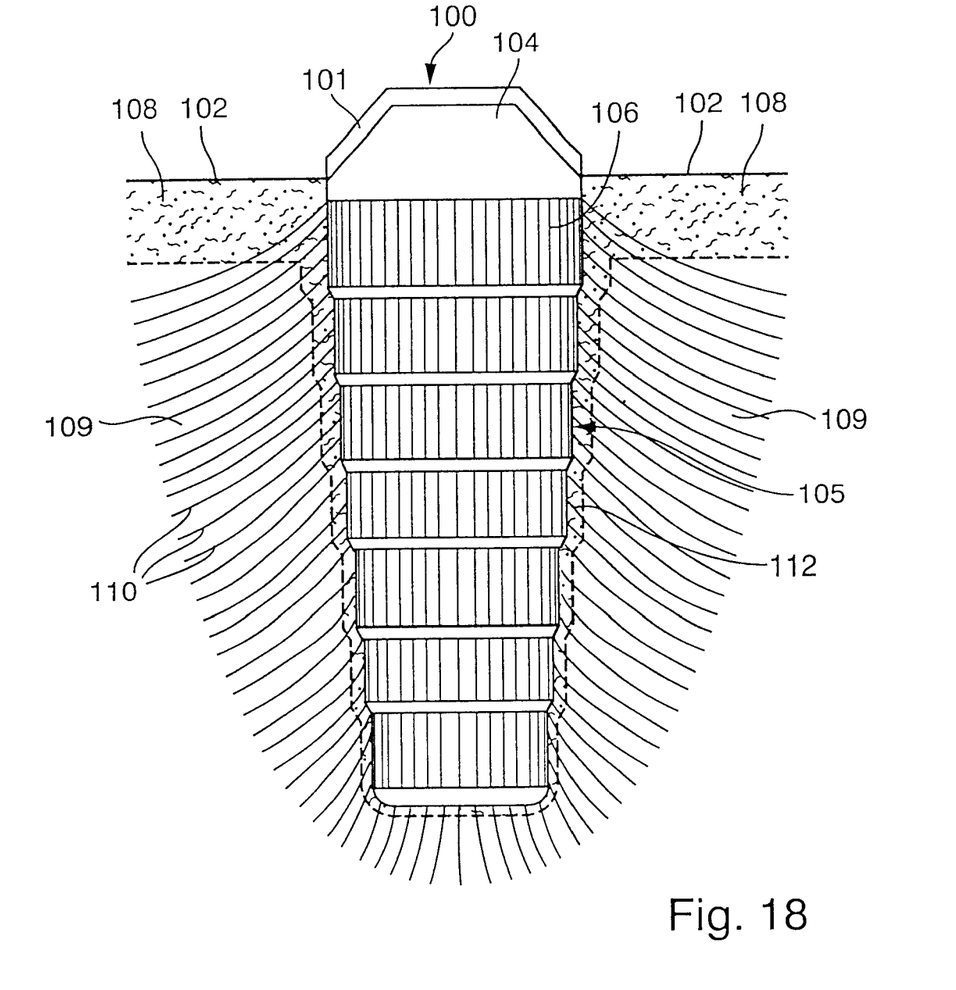

FIG. 18 shows the seat of a tooth implant 100 according to the invention in a jawbone after the healing phase. The implant 100 corresponds to that described in FIG. 14. The implant is set deep enough into the jawbone so that its head 101 lies above the top edge of the jawbone 102. The collar 104 and a part of the body 105 up to the bottom third of the first or top step 106 are in the area of the naturally compact bone 108 that is under the edge of the jawbone and neighbors the spongiosa 109 of the jawbone below. The groove-shaped surface of the implant causes the osteons 110 of the bone to collect in the grooves on the perimeter of the steps 106. This produces a tight connection between the bone and implant. The grooved structure allows the osteons to grow directly into the implant. This improves the transmission of force to the anatomical/histological bone components, in particular to the osteons, and causes a pressure-induced formation of compact bone 112 around the implant in the area of the spongiosa. This biomechanical integration shortens the healing phase for the implant and lengthens the time of the implant in the bone due to the decrease in bone resorption.

A preferred procedure for creating the tooth implant according to the invention is to manufacture the implant body in the desired shape as a cylinder, cone or stepped cone with a smooth surface using a prior art procedure such as diecasting. Material is then removed from the implant body to form numerous groove-shaped recesses in the surface of the implant body that essentially run parallel to the lengthwise axis. The groove-shaped recesses 20 can be parallel to the lengthwise axis of the implant body or parallel to its surface when the implant is conical, or at a sharp angle to it as in FIGS. 7A, 7B or 7C. The profile and the dimensions of the recesses correspond to the profile and dimensions that were described above, especially in conjunction with FIGS. 2, 5 and 6. The material removal process can advantageously be carried out with a digitally-controlled laser beam. Instead of the laser beam, a focused ion beam can be used. Alternately, the material removal process can be carried out by a precision milling machine.

The troughs or lagoons 17 are introduced into the surface of the implant body in another step. This step can consist of acid etching. The head 12, 31, 57, 96 or 101 and in certain cases the foot 33 or 80 are covered with an acid-resistant coating. A digitally controlled laser beam can also be used to create the troughs or lagoons 17. This has the advantage that the same holders and feed mechanism, the same type of tool and the same material removing processing can be used to create the groove-shaped recesses 20 and to create the troughs or lagoons 17.

Instead of directly using a laser beam or ion beam to remove material from the implant body, the same process can be used on a diecast mold that serves to create the implant using a prior art diecasting process. In this case, a negative of the described surface structures are created in a divided diecast mold that is designed as a cylinder, cone or stepped cone with a smooth surface corresponding to the shape of the implant be created.

What is claimed is:

1. A tooth implant comprising:
a rotationally symmetrical implant body having a lengthwise axis, a top and a bottom and a plurality of sections arranged along the lengthwise axis, each section having a diameter wherein section diameters diminish toward the implant body bottom to give the implant body a stepped shape; and
wherein each section of the stepped shape has a perimeter with a plurality of groove-shaped recesses therein.

2. The tooth implant according to claim 1, wherein each section is substantially cylindrical and pairs of sections are separated by radial bands that reduce the diameter of the implant body from one section to the next section.

3. The tooth implant according to claim 1, wherein a difference between a section diameter and an adjacent section diameter is in the range of 20 to 300 micrometers.

4. The tooth implant according to claim 1, wherein the groove-shaped recesses in the section perimeters have substantially equal widths.

5. The tooth implant according to claim 1, wherein the widths of the groove-shaped recesses in at least some of the section perimeters differ from each other.

6. The tooth implant according to claim 1, wherein the groove-shaped recesses extend parallel to the lengthwise axis of the implant body.

7. The tooth implant according to claim 1, wherein the groove-shaped recesses extend at an acute angle to the lengthwise axis of the implant body.

8. The tooth implant according to claim 1, comprising a first set of groove-shaped recesses which are oriented in a first direction at a sharp angle to the lengthwise axis of the implant body, and a second set of groove-shaped recesses which are oriented in a second direction at an acute angle to the lengthwise axis of the implant body and cross the first set of groove-shaped recesses.

9. The tooth implant according to claim 1, wherein each of the groove-shaped recesses has a width that is the same order of size as osteons in jawbone tissue which attaches to the groove-shaped recesses.

10. The tooth implant according to claim 9, wherein the groove-shaped recesses have widths in the range of 20 to 300 micrometers.

11. The tooth implant according to claim 9, wherein the groove-shaped recesses have depths in the range of 10 to 150 micrometers.

12. The tooth implant according to claim 1, further comprising a plurality of trough-shaped recesses which are spatially distributed in the groove-shaped recesses, the trough-shaped recesses having overall dimensions that are small in comparison with the groove-shaped recess width.

13. The tooth implant according to claim 12, wherein the trough-shaped recesses have a width of substantially three micrometers and a depth of substantially one micrometer.

14. The tooth implant according to claim 1, further comprising a collar area located at the implant body top and having a periphery with a plurality of small spatially distributed troughs in the collar periphery.

15. The tooth implant according to claim 1, further comprising a smoothly polished foot area located at the implant body bottom.

16. A tooth implant comprising:
a rotationally symmetrical implant body having a lengthwise axis, a top and a bottom and a plurality of sections arranged along the lengthwise axis, each section having a diameter;
a plurality of radial bands, each radial band being located between a pair of sections; and
wherein each section has a perimeter with a plurality of groove-shaped recesses therein, each of the groove-shaped recesses having a width that is the same order of size as osteons in jawbone tissue which attaches to the groove-shaped recesses.

17. The tooth implant according to claim 16, wherein the groove-shaped recesses extend parallel to the lengthwise axis of the implant body.

18. The tooth implant according to claim 16, wherein the groove-shaped recesses extend at an acute angle to the lengthwise axis of the implant body.

19. The tooth implant according to claim 16, comprising a first set of groove-shaped recesses that are oriented in a first direction at an acute angle to the lengthwise axis of the implant body, and a second set of groove-shaped recesses which are oriented in a second direction at an acute angle to the lengthwise axis of the implant body and cross the first set of groove-shaped recesses.

20. The tooth implant according to claim 16, wherein the groove-shaped recesses in the section perimeters have substantially equal widths.

21. The tooth implant according to claim 16, wherein the widths of the groove-shaped recesses in at least some of the section perimeters differ from each other.

22. The tooth implant according to claim 16, wherein the groove-shaped recesses have dimensions that differ from section to section over a length of the implant body, and wherein the dimensions are adapted to match density variations of bone tissue which occur in a jaw over a depth equal to the length of the implant body.

23. The tooth implant according to claim 22, wherein a difference between the groove-shaped recess width in a section located toward the implant body bottom and the groove-shaped recess width in a previous section is within a range of 10 to 150 micrometers.

24. The tooth implant according to claim 16, wherein the groove-shaped recesses have a width in the range of 20 to 300 micrometers.

25. The tooth implant according to claim 24, wherein the groove-shaped recesses have a depth in the range of 10 to 150 micrometers.

26. The tooth implant according to claim 16, wherein each of the sections has a frustro-conical shape with a diameter that decreases toward the implant body bottom so that the implant body has a conical shape.

27. The tooth implant according to claim 26, wherein each of the radial bands is formed by a step between the sections.

28. The tooth implant according to claim 16, further comprising a plurality of trough-shaped recesses that are spatially distributed in the groove-shaped recesses, said trough-shaped recesses are small in comparison with the groove-shaped recesses.

29. The tooth implant according to claim 28, wherein the trough-shaped recesses have a width of substantially three micrometers and a depth of substantially one micrometer.

30. The tooth implant according to claim 16, further comprising a collar area located on the implant body between the groove-shaped recesses and an implant head and having a periphery with a plurality of small spatially distributed troughs in the collar periphery.

31. The tooth implant according to claim 16, further comprising a smoothly polished foot area at the implant body bottom.

32. A tooth implant for implantation in jawbone tissue having osteons which attach to the implant, and comprising:
a rotationally symmetrical implant body having a top, a bottom, a periphery and a lengthwise axis; and
a plurality of groove-shaped recesses located in the periphery, said recesses extending along the lengthwise axis, and having a width with an order of size that corresponds to an order of size of the osteons.

33. A tooth implant according to claim 32 wherein the groove-shaped recesses extend parallel to the lengthwise axis.

34. A tooth implant according to claim 32 wherein the groove-shaped recesses extend at an acute angle to the lengthwise axis.

35. The tooth implant according to claim 32, comprising a first set of groove-shaped recesses which are oriented in a first direction at an acute angle to the lengthwise axis, and a second set of groove-shaped recesses which are oriented in a second direction at an acute angle to the lengthwise axis and which cross the groove-shaped recesses of the first set.

36. The tooth implant according to claim 32, wherein the groove-shaped recesses have a width in the range of 20 to 300 micrometers.

37. The tooth implant according to claim 32, wherein the groove-shaped recesses have a depth in the range of 10 to 150 micrometers.

38. The tooth implant according to claim 32, further comprising a plurality of trough-shaped recesses that are spatially distributed in the groove-shaped recesses, said trough-shaped recesses being small in overall dimensions in comparison with dimensions of the groove-shaped recesses.

39. The tooth implant according to claim 38, wherein the trough-shaped recesses have a width of substantially three micrometers and a depth of substantially one micrometer.

40. The tooth implant according to claim 32, comprising a collar area located on the implant body between the groove-shaped recesses and an implant head and having a periphery with a plurality of small spatially distributed troughs in the collar periphery.

41. The tooth implant according to claim 32, further comprising a smoothly polished foot area at the implant body bottom.

42. A bone implant for insertion into bone tissue in a human body having osteons that attach to the implant, comprising:
an implant body having a lengthwise axis and a periphery with a plurality of groove-shaped recesses therein extending along the lengthwise axis and having dimensions with an order of size that corresponds to an order of size of the osteons.

43. A bone implant according to claim 42 wherein the groove-shaped recesses extend parallel to the lengthwise axis.

44. A bone implant according to claim 42 wherein the groove-shaped recesses extend at an acute angle to the lengthwise axis.

45. The bone implant according to claim 42, comprising a first set of groove-shaped recesses which are oriented in a first direction at an acute angle to the lengthwise axis, and a second set of groove-shaped recesses which are oriented in a second direction at an acute angle to the lengthwise axis and cross the groove-shaped recesses of the first set.

46. The bone implant according to claim 42, wherein the groove-shaped recesses have a width in the range of 20 to 300 micrometers.

47. The bone implant according to claim 42, wherein the groove-shaped recesses have a depth in the range of 10 to 150 micrometers.

48. The bone implant according to claim 42, further comprising a plurality of trough-shaped recesses that are spatially distributed in the groove-shaped recesses, said trough-shaped recesses having dimensions that are small in comparison with dimensions of the groove-shaped recesses.

49. The bone implant according to claim 47, wherein the trough-shaped recesses have a width of substantially three micrometers and a depth of substantially one micrometer.

50. A method of manufacturing a tooth implant with a pre-shaped rotationally symmetrical implant body having a top, a bottom, a length, a lengthwise axis and rough surface with a plurality of groove-shaped recesses therein, comprising:
(a) preforming the implant body with a plurality of rotationally symmetric sections along the lengthwise axis wherein the sections have peripheries and the diameters of the implant body sections decrease toward the implant body bottom to form a stepped shape; and
(b) forming the groove-shaped recesses into the peripheries of each of the sections.

51. The method according to claim 50, wherein the groove-shaped recesses have substantially the same width over the implant body length.

52. The method according to claim 50, wherein step (b) comprises forming over the implant body length, in at least some of the section peripheries, groove-shaped recesses which differ from each other.

53. The method according to claim 52, wherein step (b) comprises forming over the implant body length, in at least some of the section peripheries, groove-shaped recesses which differ in size from each other.

54. The method according to claim 50, wherein step (b) comprises forming the groove-shaped recesses parallel to the implant body lengthwise axis.

55. The method according to claim 50, wherein step (b) comprises forming the groove-shaped recesses at an acute angle to the implant body lengthwise axis.

56. The method according to claim 50, wherein step (b) comprises producing a first set of groove-shaped recesses in a first direction at an acute angle to the lengthwise axis of the implant body, and producing a second set of groove-shaped recesses in a second direction at an acute angle to the lengthwise axis of the implant body that cross the first set of groove-shaped recesses.

57. The method according to the claim 50, further comprising:
(c) producing a plurality of spatially distributed small troughs in said groove-shaped recesses by removing material therefrom.

58. The method according to claim 57, wherein step (c) comprises removing material by etching.

59. The method according to the claim 50, further comprising:
(d) forming a collar area at the implant body top, the collar area having a periphery; and
(e) producing a plurality of spatially distributed small troughs in the collar area periphery by removing material therefrom.

60. The method according to claim 59, wherein the troughs have a width of substantially three micrometers and a depth of substantially one micrometer.

61. The method according to claim 50, wherein step (b) comprises forming the groove-shaped recesses by removing material with a laser beam.

62. A method of manufacturing a tooth implant for implantation into jawbone tissue with osteons therein that attach to the implant, the implant having a pre-shaped rotationally symmetrical body with a top, a bottom, a length, a lengthwise axis and a rough surface on which a plurality of groove-shaped recesses are formed, the method comprising:

(a) dividing the implant body surface in the direction of the lengthwise axis into a number of sections, each section having a periphery;

(b) separating pairs of the sections from each other by radial extending bands;

(c) producing a plurality of groove-shaped recesses in the periphery of each of the sections by removing material therefrom, wherein the groove-shaped recesses extend along the lengthwise axis and have an order of size that corresponds to an order of size of the osteons.

63. The method according to claim 62, wherein step (c) comprises producing the groove-shaped recesses parallel to the implant body lengthwise axis.

64. The method according to claim 62, wherein step (c) comprises producing the groove-shaped recesses at an acute angle to the implant body lengthwise axis.

65. The method according to claim 62, wherein the groove-shaped recesses in said sections have essentially a same width over the implant body length.

66. The method according to claim 63, wherein step (c) comprises producing over the implant body length in at least some of the sections, groove-shaped recesses which differ from each other.

67. The method according to claim 66, wherein step (c) comprises producing over the implant body length in at least some of the sections, groove-shaped recesses which differ from each other in size.

68. The method according to claim 63, wherein step (c) comprises producing a first set of groove-shaped recesses in a first direction at an acute angle to the implant body lengthwise axis, and producing a second set of groove-shaped recesses in a second direction at an acute angle to the implant body lengthwise axis and that cross the first set of groove-shaped recesses.

69. The method according to claim 63, comprising:

(d) producing a plurality of spatially distributed small troughs in the groove-shaped recesses by removing material therefrom.

70. The method according to claim 63, wherein step (a) comprises preforming the sections into frustro-conical shapes with diameter that decrease toward the implant body bottom so that the implant body has a conical shape.

71. The method according to claim 63, wherein in step (c) the groove-shaped recesses do not extend across the radial extending bands.

72. The method according to claim 63, wherein each of the sections is cylindrical and wherein step (b) comprises separating the sections with radial extending bands that have a width and reduce in diameter across the width.

73. The method according to claim 63, wherein the groove-shaped recesses have a width in the range of 20 to 300 micrometers, and a depth in the range of 10 to 150 micrometers.

74. The method according to claim 63, comprising:

(e) producing a plurality of trough-shaped recesses in the groove-shaped recesses by removing material therefrom, the trough-shaped recesses being small in comparison with the groove-shaped recesses and spatially distributed over the groove-shaped recesses.

75. The method according to claim 74, wherein step (e) comprises producing the trough-shaped recesses by etching.

76. The method according to claim 75, wherein the trough-shaped recesses have a width of substantially three micrometers and a depth of substantially one micrometer.

77. The method according to claim 63, wherein, in step (c), material is removed with a laser beam.

* * * * *

UNITED STATES PATENT AND TRADEMARK OFFICE
CERTIFICATE OF CORRECTION

PATENT NO.     : 6,364,663 B1
DATED          : April 2, 2002
INVENTOR(S)    : Wolfgang Dinkelacker It is certified that error appears in the above-identified patent and that said Letters Patent is hereby corrected as shown below:

Column 10,
Line 9, replace "claim 47" with -- claim 48 --;

Column 11,
Lines 27 and 36, replace "claim 63" with -- claim 62 --; and

Column 12,
Lines 5, 9, 13, 16, 20, 24 and 35, replace "claim 63" with -- claim 62 --.

Signed and Sealed this

Twenty-fourth Day of May, 2005

JON W. DUDAS
*Director of the United States Patent and Trademark Office*